US005801280A

United States Patent [19]

Yoneyoshi et al.

[11] Patent Number: 5,801,280
[45] Date of Patent: Sep. 1, 1998

[54] PROCESSES FOR PREPARING OPTICALLY ACTIVE ALCOHOLS AND OPTICALLY ACTIVE AMINES

[75] Inventors: Yukio Yoneyoshi, Shiga; Naoto Konya, Chiba; Gohfu Suzukamo, Osaka; Masashi Kamitamari, Osaka; Takashi Miyawaki, Osaka, all of Japan

[73] Assignee: Sumitomo Chemical Company, Limited, Osaka, Japan

[21] Appl. No.: 628,154

[22] Filed: Apr. 5, 1996

[30] Foreign Application Priority Data

| Apr. 7, 1995 | [JP] | Japan | 7-082919 |
| Apr. 7, 1995 | [JP] | Japan | 7-082920 |
| Apr. 7, 1995 | [JP] | Japan | 7-082958 |
| Apr. 13, 1995 | [JP] | Japan | 7-088450 |
| Jun. 22, 1995 | [JP] | Japan | 7-156071 |

[51] Int. Cl.$^6$ ............................................. C07C 209/40
[52] U.S. Cl. ........................... 564/415; 564/489; 564/413
[58] Field of Search ........................... 564/415, 489, 564/413

[56] References Cited

U.S. PATENT DOCUMENTS

| 5,200,561 | 4/1993 | Konya et al. | 564/373 |
| 5,442,118 | 8/1995 | Gao et al. | 564/356 |
| 5,574,186 | 11/1996 | Boudreau et al. | 564/393 |

FOREIGN PATENT DOCUMENTS

| 0485069 | 5/1992 | European Pat. Off. . |
| 0641786 | 3/1995 | European Pat. Off. . |
| 7109231 | 4/1995 | Japan . |

OTHER PUBLICATIONS

S. Itsuno et al., *J. Chem. Soc. Perkin Trans 1*, 1985, pp. 2039–2044.

Tetrahedron Letters, vol. 29, No. 2, 1988, Oxford GB, pp. 223–224, Y. Sakito et al.: "Asymmetric reduction of oxime ethers. Distinction of anti and syn isomers leading to enantiomeric amines".

Database WPI Section Ch, Week 9528, Derwent Publications Ltd., London, GB; Class B03, AN 95-209417 (1995).

*Primary Examiner*—Brian M. Burn
*Attorney, Agent, or Firm*—Birch, Stewart, Kolasch & Birch, LLP

[57] ABSTRACT

A process for preparing an optically active alcohol by reacting a prochiral ketone corresponding to the optically active alcohol and an acid with a mixture of (1) a boron-containing compound selected from the group consisting of i) a borane compound which is obtained from an optically active β-aminoalcohol and a boron hydride; or obtained from the optically active β-aminoalcohol, a metal borohydride and an acid and ii) an optically active oxazaborolidine and (2) a metal borohydride; and a process for preparing an optically active amine by reacting an oxime derivative and an acid with a mixture of (1) a boron-containing compound selected from the group consisting of i) a borane compound which is obtained from an optically active β-aminoalcohol and a boron hydride, or obtained from said optically active β-aminoalcohol, a metal borohydride and an acid and ii) an optically active oxazaborolidine, and (2) a metal borohydride.

9 Claims, No Drawings

PROCESSES FOR PREPARING OPTICALLY ACTIVE ALCOHOLS AND OPTICALLY ACTIVE AMINES

BACKGROUND OF THE INVENTION

1. Field of the Invention

The present invention relates to a process for preparing an optically active alcohol and a process for preparing an optically active amine.

2. Description of the Related Art

As a process for preparing an optically active alcohol, for example, there is known a process comprising reacting an optically active β-aminoalcohol and a borane in an amount of two moles per one mole of said aminoalcohol, and then reacting a prochiral ketone in an amount of 0.8 mole per one mole of said aminoalcohol with a reaction product (see, for example, J. Chem. Soc. PERKIN TRANS. I., 2039 (1985)).

However, this process has a drawback that a large amount of the expensive borane should be used.

To solve such drawback, JP-A-7-109231 discloses a process for preparing an optically active alcohol using a metal borohydride which is cheap and easily available in an industrial scale, that is, a process comprising reacting a mixture of a 2-substituted oxazaborolidine having substituents on a boron atom and a metal borohydride with an acid, and then reacting a prochiral ketone with a reaction product to obtain an optically active alcohol. But, an optical purity of the produced optically active alcohol is unsatisfactory, and further improvement of the process has been desired.

As a process for preparing an optically active amine, there is proposed a process comprising reacting an optically active β-aminoalcohol with a borane, and then reacting a syn or anti-form of an oxime derivative with a reaction product, whereby an optically active amine having a desired absolute configuration is prepared (see JP-A-63-99041 and Tetrahedron Lett., 29223 (1988).

However, this process has a drawback that a large amount of an expensive borane should be used.

To solve such drawback, JP-A-2-311446 and JP-A-5-9158 disclose a process for preparing an optically active amine using a metal borohydride which is cheap and easily available in an industrial scale, that is, a process comprising reacting an optically active β-aminoalcohol with a metal borohydride and an acid, and then reacting an oxime derivative with a reaction product.

SUMMARY OF THE INVENTION

An object of the present invention is to provide a process for preparing an optically active alcohol having an increased optical purity effectively even in an industrial scale while reducing an amount of a used metal borohydride or boron hydride as a hydrogen source.

Another object of the present invention is to provide a process for preparing an optically active amine having an increased optical purity effectively even in an industrial scale while reducing an amount of a used metal borohydride or boron hydride as a hydrogen source.

According to a first aspect of the present invention, there is provided a process for preparing an optically active alcohol comprising reacting a prochiral ketone which corresponds to the optically active alcohol and an acid with a mixture which comprises (1) a boron-containing compound selected from the group consisting of i) a borane compound which is obtained from an optically active β-aminoalcohol of the formula (I):

wherein $R^1$ is a hydrogen atom, a lower alkyl group or an aralkyl group which may have at least one substituent, $R^2$, $R^3$, $R^4$ and $R^5$ represent independently each other a hydrogen atom, a lower alkyl group, an aryl group which may have at least one substituent, or an aralkyl group which may have a substituent, provided that $R^4$ and $R^5$ are different, that $R^3$ and $R^5$ may together form a lower alkylene group, or that $R^3$ and $R^4$ may together form a lower alkylene group which may have optionally a substituent or with which a benzene ring is condensed, and * stands for an asymmetric carbon atom, and a boron hydride; or obtained from said optically active β-amino-alcohol (I), a metal borohydride and an acid, and ii) an optically active oxazaborolidine of the formula (II):

wherein $R^1$, $R^2$, $R^3$, $R^4$, $R^5$ and * are the same as defined above, and $R^6$ is a hydrogen atom, a halogen atom, an alkyl group which may be substituted by at least one halogen atom, an aryl group which may have at least one substituent or an aralkyl group which may have at least one substituent, and (2) a metal borohydride.

According to a second aspect of the present invention, there is provided a process for preparing an optically active amine of the formula:(III):

wherein $R^7$ and $R^8$ are different and represent an alkyl group which may have at least one substituent, an aryl group which may have at least one substituent or an aralkyl group which may have at least one substituent, or $R^7$ and $R^8$ form, together with the carbon atom bonded to the amino group, a ring or condensed ring which may have a hetero atom, and * is the same as defined above comprising reacting an oxime derivative of the formula (IV):

wherein $R^7$ and $R^8$ are the same as defined above, and $R^9$ is an alkyl group, an aralkyl group or an alkyl-substituted silyl group and an acid with a mixture which comprises (1) a boron-containing compound selected from the group consisting of i) a borane compound which is obtained from an optically active β-aminoalcohol of the formula (I)

and a boron hydride, or obtained from said optically active β-aminoalcohol (I), a metal borohydride and an acid, and ii) an optically active oxazaborolidine of the formula (II) and (2) a metal borohydride.

The oxime derivative (IV) may be a syn-form, an anti-form or a mixture thereof which is rich in one of them.

DETAILED DESCRIPTION OF THE INVENTION

Preparation of a mixture of a borane compound and metal borohydride $R^1$ in the optically active β-aminoalcohol of the formula (I) is a hydrogen atom, a straight or branched lower alkyl group having usually 1 to 8 carbon atom, preferably 1 to 5 carbon atoms (e.g. methyl, ethyl, n-propyl, isopropyl, n-butyl, isobutyl, sec.-butyl, tert.-butyl, pentyl, etc.), or an aralkyl group having usually 7 to 15 carbon atom, preferably 7 to 12 carbon atoms (e.g. benzyl, phenethyl, methylbenzyl, etc.) which may be substituted with a lower ($C_1$–$C_5$) alkyl or alkoxy group (e.g. methyl, ethyl, n-propyl, isopropyl, n-butyl, isobutyl, sec.-butyl, tert.-butyl, pentyl, methoxy, ethoxy, propoxy, butoxy, pentoxy, etc.).

$R^2$, $R^3$, $R^4$ and $R^5$ represent independently each other a hydrogen atom, a lower alkyl group having usually 1 to 8 carbon atom, preferably 1 to 5 carbon atoms (e.g. methyl, ethyl, n-propyl, isopropyl, n-butyl, isobutyl, sec.-butyl, tert.-butyl, pentyl, etc.), an aryl group having 6 to 12 carbon atoms, preferably 6 to 11 carbon atoms (e.g. phenyl, 1-naphthyl, 2-naphthyl, etc.), or an aralkyl group having usually 7 to 12 carbon atoms (e.g. benzyl, phenethyl, methylbenzyl, etc.). The aryl or aralkyl group may be substituted with a lower alkyl or alkoxy group which may be the same as exemplified above. $R^4$ and $R^5$ are not the same. $R^1$ and $R^5$ may together form a lower alkylene group such as methylene, dimethylene, trimethylene, tetramethylene, etc. $R^3$ and $R^4$ may together form a lower alkylene group which may have optionally a substituent or with which a benzene ring is condensed, such as trimethylene, tetramethylene, pentamethylene, o-phenylenemethylene, o-phenylenedimethylene, etc.

Specific examples of the optically active β-aminoalcohol (I) are optically active norephedrine, ephedrine, 2-amino-1-(2,5-dimethylphenyl)-1-propanol, 2-amino-1-(2,5-dimethoxyphenyl)-1-propanol, 2-amino-1-(2,5-diethoxyphenyl)-1-propanol, 2-amino-1-(2,5-dipropoxyphenyl)-1-propanol, 2-amino-1-(2-methoxyphenyl)-1-propanol, 2-amino-1-(2-ethoxyphenyl)-1-propanol, 2-amino-1-(2-propoxyphenyl)-1-propanol, 2-amino-1-(2-methylphenyl)-1-propanol, 2-amino-1-(2-methoxy-5-methylphenyl)-1-propanol, 2-amino-1-(4-methoxy-2-methylphenyl)-1-propanol, 2-amino-1-(2-ethoxy-5-methylphenyl)-1-propanol, 2-amino-1-(2,4-dimethylphenyl)-1-propanol, 2-amino-1-(2,4,6-trimethylphenyl)-1-propanol, 2-amino-1-(1-naphthyl)-1-propanol, 2-amino-1-(2-naphthyl)-1-propanol, 2-amino-1,2-diphenylethanol, 2-amino-1,1-diphenyl-1-propanol, 2-amino-1,1-diphenyl-3-methyl-1-butanol, 2-amino-1,1-diphenyl-4-methyl-1-propanol, 2-amino-1,1-diphenyl-1-butanol, 2-amino-1,1,3-triphenyl-1-propanol, 2-amino-1,1,2-triphenyl-1-ethanol, 2-amino-3-methyl-1-butanol, 2-amino-4-methyl-1-pentanol, 2-amino-1-propanol, 2-amino-3-phenyl-1-propanol, 2-amino-2-phenyl-1-ethanol, etc., and their N-lower alkyl or N-aralkyl derivatives; 2-pyrrolidinemethanol, α,α-diphenyl-2-pyrrolidinemethanol, 2-piperidinemethanol, α,α-diphenyl-2-piperidinemethanol, 2-aziridinemethanol, α,α-diphenyl-2-azetizinemethanol, 2-azetizinemethanol, α,α-diphenyl-2-azetizinemethanol, 2-aminocyclopentan-1-ol, 2-aminocyclohexan-1-ol, 1-aminoindan-2-ol, and so on.

Examples of the boron hydride are diborane, borane-tetrahydrofuran complex, borane-dioxane complex, borane-dimethylsulfide complex, borane-thioxane complex, and so on.

Examples of the metal borohydride are lithium borohydride, sodium borohydride, potassium borohydride, zinc borohydride, and so on. Among them, sodium borohydride is preferred.

The metal borohydride used in the preparation of the borane compound and that used in the reduction of the prochiral ketone or the oxime derivative (IV) are usually the same, while they may be different.

Examples of the acid are Brønsted acids such as sulfuric acid, acetic acid, phosphoric acid, methanesulfonic acid, p-toluenesulfonic acid, hydrogen chloride, etc.; and Lewis acids such as zinc chloride, boron trifluoride, aluminum chloride, aluminum bromide, titanium tetrachloride, tin tetrachloride, tin trichloride, iodine, etc.

The acid used in the preparation of the borane compound and that used in the reduction of the prochiral ketone or the oxime derivative (IV) are usually the same, while they may be different.

The preparation of the borane compound and the reduction of the prochiral ketone or the oxime derivative (IV) are usually performed in the presence of a solvent. The solvent used in the preparation of the borane compound and that used in the reduction of the prochiral ketone or the oxime derivative (IV) are usually the same, while they may be different.

Examples of the solvent are ethers (e.g. dioxane, 1,3-dioxolane, tetrahydrofuran, diglyme, etc.), sulfides (e.g. dimethylsulfide, diethylsulfide, etc.), and mixtures thereof, and mixtures of the above solvent and a hydrocarbon (e.g. benzene, toluene, xylene, chlorobenzene, 1,2-dichloroethane, etc.).

An amount of the solvent is usually from 1 to 50 times the weight of the prochiral ketone or the oxime derivative (IV).

In the preparation of the borane compound, in general, the boron hydride is added to the mixture of the optically active β-aminoalcohol (I) and the solvent, or the acid is added to the mixture of the optically active β-aminoalcohol (I), the metal borohydride and the solvent. The boron hydride or the acid may be used as a mixture in the solvent.

In general, the boron hydride or the metal borohydride is used in an amount of 0.8 to 2 moles in terms of the boron atom per one mole of the optically active β-aminoalcohol (I). When the metal borohydride is used, it may be added, at this stage, in an amount sufficient for performing the reaction with the optically active β-aminoalcohol (I) and also the reduction of the prochiral ketone or the oxime derivative (IV). The metal borohydride is more preferably used than the boron hydride.

The acid is used usually in an amount of 0.8 to 2.1 equivalents of the optically active β-aminoalcohol (I).

In general, an amount of the metal borohydride which contributes to the synthesis of the borane compound is determined by the amount of the acid. Theoretically, an excessive portion of the metal borohydride in relation to the acid will form a mixture with the borane compound.

A temperature at which the boron hydride is added is usually from −20° to +100° C., preferably from 0° to 80° C.

After the addition of the boron hydride, the reaction mixture is preferably stirred at the same temperature for 0.1 to 20 hours.

A temperature at which the acid is added is usually from $-20°$ to $+100°$ C., preferably from $0°$ to $80°$ C. After the addition of the acid, the reaction mixture is preferably stirred at the same temperature for 0.1 to 10 hours.

In the reduction of the prochiral ketone, an amount of the optically active β-aminoalcohol (I) is usually from 0.005 to 0.5 mole, preferably from 0.01 to 0.4 mole per one mole of the prochiral ketone. In the reduction of the oxime derivative (IV), an amount of the optically active β-aminoalcohol (I) is usually from 0.01 to 1.1 moles, preferably from 0.01 to 0.9 mole, more preferably 0.03 to 0.9 mole per one mole of the oxime derivative (IV).

In a case where the metal borohydride is added in the preparation step of the borane compound in an amount sufficient for performing the reaction with the optically active β-aminoalcohol (I) and also the reduction of the prochiral ketone or the oxime derivative (IV), the mixture of the borane compound and the metal borohydride is obtained, while, in other case, such mixture is obtained by the addition of the metal borohydride to the resulting borane compound.

When the metal borohydride is additionally added, an amount of the metal borohydride in the mixture with the borane compound is usually from 0.3 to 3 moles, preferably from 0.5 to 2 moles in terms of the boron atom per one mole of the prochiral ketone in the case of the reduction of the prochiral ketone. The reaction proceeds sufficiently when this amount is from 0.5 to 1 mole. In the case of the reduction of the oxime derivative, the additional amount of the metal borohydride is usually from 0.5 to 2.1 moles, preferably from 0.8 to 1.5 moles in terms of the boron atom per one mole of the oxime derivative (IV).

Preparation of a mixture of a optically active oxazaborolidine (II) and a metal borohydride Examples of the alkyl, aralkyl and aryl groups for $R^1$, $R^2$, $R^3$, $R^4$ and $R^5$, and examples of the alkylene group formed from $R^1$ and $R^5$ or $R^3$ and $R^4$ in the optically active oxazaborolidine (II) are the same as those exemplified in connection with the optically active β-aminoalcohol (I).

Examples of the lower alkyl group for $R^6$ are the same as those for $R^2$ and so on, that is, an alkyl group having usually 1 to 8 carbon atoms which may be substituted with 1 to 6 halogen atoms (e.g. hexyl, cyclohexyl, heptyl, 2-ethylhexyl, octyl, 1-chloroethyl, 1-bromoethyl, 1-fluoroethyl, 2-fluoroethyl, 3-chloropropyl, 3,3,3-trifluoropropyl. Examples of the aryl group are an aryl group having usually 6 to 12 carbon atoms, preferably 6 to 10 carbon atoms (e.g. phenyl, 1-naphthyl, 2-naphthyl, etc.), an aryl group substituted with at least one alkyl group having usually 1 to 8 carbon atoms (e.g. o-, m- or p-methylphenyl, o-, m- or p-ethylphenyl, o-, m- or p-butylphenyl, 2,3-, 2,4-, 2,5-, 2,6-, 3,4- or 3,5-dimethylphenyl, etc.), an aryl group substituted with at least one alkoxy group having usually 1 to 8 carbon atoms (e.g. o-, m- or p-methoxyphenyl, o-, m- or p-ethoxyphenyl, o-, m- or p-propoxyphenyl, 2,3-, 2,4-, 2,5-, 2,6-, 3,4- or 3,5-dimethoxyphenyl, etc.), an aryl group substituted with at least one halogen atom (e.g. o-, m- or p-chlorophenyl, o-, m- or p-bromophenyl, o-, m- or p-fluorophenyl, 2,3-, 2,4-, 2,5-, 2,6-, 3,4- or 3,5-difluorophenyl, 2,3,4-, 2,3,5-, 2,3,6-, 2,4,5-, 2,4,6-, or 3,4,5-trifluorophenyl, etc.), an aryl group substituted with at least one halogen atom and at least one alkyl group (e.g. 4-bromo-3,5-dimethylphenyl, 4-bromo-2,6-dimethylphenyl, 4-fluoro-3,5-dimethylphenyl, etc.), an aryl group substituted with at least one halogen atom and at least one alkoxy group (e.g. 2-chloro-5-methoxyphenyl, 2-bromo-5-methoxyphenyl, 2-fluoro-5-methoxyphenyl, 3-bromo-5-methoxyphenyl, 4-ethoxy-2,3-difluorophenyl, etc.), and an aryl group substituted with a halogenated alkyl group (e.g. 2-(chloromethyl)phenyl, 2-(bromomethyl)phenyl, 2-(fluoromethyl)phenyl, 3-(trifluoromethyl)phenyl, o-, m- or p-(1-chloroethyl)phenyl, o-, m- or p-(1-bromoethyl)phenyl, o-, m- or p-(3-chloropropyl)phenyl, 2-bromomethyl-6-methylphenyl, etc.). Examples of the aralkyl group are an aralkyl group having usually 7 to 12 carbon atoms, preferably 7 to 10 carbon atoms (e.g. benzyl, etc.), an aralkyl group substituted with at least one alkyl or alkoxy group having 8 to 13 carbon atoms (e.g. o-, m- or p-tolylmethyl, o-, m- or p-ethylbenzyl, o-, m- or p-methoxybenzyl, o-, m- or p-ethoxybenzyl, 2,3-, 2,4-, 2,5-, 2,6-, 3,4- or 3,5-dimethylbenzyl, (2,3-, 2,4-, 2,5-, 2,6-, 3,4- or 3,5-dimethylphenyl)ethylalkyl. Examples of the halogen atom are fluorine, chlorine and bromine.

Specific examples of the optically active oxazaborolidine (II) are optically active 1,3,2-(4-methyl-5-phenyl)oxazaborolidine, 1,3,2-(2,4-dimethyl-5-phenyl)oxazaborolidine, 1,3,2-(2-ethyl-4-methyl-5-phenyl)oxazaborolidine, 1,3,2-(2-propyl-4-methyl-5-phenyl)oxazaborolidine, 1,3,2-(2-butyl-4-methyl-5-phenyl)oxazaborolidine, 1,3,2-(4-methyl-2,5-diphenyl)oxazaborolidine, 1,3,2-(2-(o-fluorophenyl)-4-methyl-5-phenyl)oxazaborolidine, 1,3,2-(2-(m-fluorophenyl)-4-methyl-5-phenyl)oxazaborolidine, 1,3,2-(2-(p-fluorophenyl)-4-methyl-5-phenyl)oxazaborolidine, 1,3,2-(2-(2,4-difluorophenyl)-4-methyl-5-phenyl)oxazaborolidine, 1,3,2-(2-(2,5-difluorophenyl)-4-methyl-5-phenyl)oxazaborolidine, 1,3,2-(2-(2,6-difluorophenyl)-4-methyl-5-phenyl)oxazaborolidine, 1,3,2-(2-(2-chlorophenyl)-4-methyl-5-phenyl)oxazaborolidine, 1,3,2-(2-(3-chlorophenyl)-4-methyl-5-phenyl)oxazaborolidine, 1,3,2-(2-(2,3-dichlorophenyl)-4-methyl-5-phenyl)oxazaborolidine, 1,3,2-(2-(2,6-dichlorophenyl)-4-methyl-5-phenyl)oxazaborolidine, 1,3,2-(2-(3,5-dichlorophenyl)-4-methyl-5-phenyl)oxazaborolidine, 1,3,2-(2-(o-methoxyphenyl)-4-methyl-5-phenyl)oxazaborolidine, 1,3,2-(2-(m-methoxyphenyl)-4-methyl-5-phenyl)oxazaborolidine, 1,3,2-(2-(p-methoxyphenyl)-4-methyl-5-phenyl)oxazaborolidine, 1,3,2-(2-(2,5-dimethoxyphenyl)-4-methyl-5-phenyl)oxazaborolidine, 1,3,2-(2-(o-tolyl)-4-methyl-5-phenyl)oxazaborolidine, 1,3,2-(2-(m-tolyl)-4-methyl-5-phenyl)oxazaborolidine, 1,3,2-(2-(p-tolyl)-4-methyl-5-phenyl)oxazaborolidine, 1,3,2-(2-(2,5-dimethylphenyl)-4-methyl-5-phenyl)oxazaborolidine, 1,3,2-(4,5-diphenyl)oxazaborolidine, 1,3,2-(2-methyl-4,5-diphenyl)oxazaborolidine, 1,3,2-(2-methyl-4,5-di(2-naphthyl)oxazaborolidine, 1,3,2-(4,5-di(2-naphthyl))oxazaborolidine, 1,3,2-(2-methyl-4-(2-methylpropyl)-5-phenyl)oxazaborolidine, 1,3,2-(4-(2-methylpropyl)-5-phenyl)oxazaborolidine, 1,3,2-(2-methyl-4-(1-methylpropyl)-5-phenyl)oxazaborolidine, 1,3,2-(4-(1-methylpropyl)-5-phenyl)oxazaborolidine, 1,3,2-(2-methyl-4-(1-methylethyl)-5-phenyl)oxazaborolidine, 1,3,2-(4-(1-methylethyl)-5-phenyl)oxazaborolidine, 1,3,2-(2-methyl-4-(1,1-dimethylethyl)-5-phenyl)oxazaborolidine, 1,3,2-(4-(1,1-dimethylethyl)-5-phenyl)oxazaborolidine, 1,3,2-(2-methyl-4-(phenylmethyl)-5-phenyl)oxazaborolidine, 1,3,2-(4-(phenylmethyl)-5-phenyl)oxazaborolidine, 1,3,2-(2-methyl-4-(phenyl-5-(p-tolyl))oxazaborolidine, 1,3,2-(4-phenyl-5-(p-tolyl))oxazaborolidine, 1,3,2-(2,4-dimethyl-5-(2,5-dimethylphenyl))oxazaborolidine, 1,3,2-(4-methyl-5-(2,5-dimethylphenyl))oxazaborolidine, 1,3,2-(2,4-dimethyl- 5-(2,5-dimethoxyphenyl))oxazaborolidine, 1,3,2-(4-methyl-5-(2,5-dimethoxyphenyl))oxazaborolidine, 1,3,2-(2-methyl-4-phenyl)oxazaborolidine, 1,3,2-(4-phenyl)oxazaborolidine, 1,3,2-(2,4-diphenyl)oxazaborolidine, 1,3,2-(2,4-dimethyl)oxazaborolidine, 1,3,2-(4-methyl)oxazaborolidine, 1,3,2-(4-ethyl)oxazaborolidine, 1,3,2-(2-methyl-4-ethyl)oxazaborolidine, 1,3,2-(4-propyl)oxazaborolidine, 1,3,2-(2-methyl-4-propyl)oxazaborolidine, 1,3,2-(4-isopropyl)oxazaborolidine, 1,3,2-(2-methyl-4-isopropyl)oxazaborolidine, 1,3,2-(2-methyl-4-(1-methylpropyl))oxazaborolidine, 1,3,2-(4-(1-methylpropyl))oxazaborolidine, 1,3,2-(2-methyl-4-(2-methylpropyl))oxazaborolidine, 1,3,2-(4-(2-methylpropyl))oxazaborolidine, 1,3,2-(2-methyl-4-(tert.-butyl))oxazaborolidine, 1,3,2-(4-(tert.-butyl))oxazaborolidine, 1,3,2-(2-methyl-4,5,5-triphenyl)oxazaborolidine, 1,3,2-(4,5,5-triphenyl)oxazaborolidine, 1,3,2-(4-benzyl)oxazaborolidine, 1,3,2-(2-methyl-4-benzyl)oxazaborolidine, 1,3,2-(2-methyl-4-benzyl-5,5-diphenyl)oxazaborolidine, 1,3,2-(4-benzyl-5,5-diphenyl)oxazaborolidine, 1,3,2-(4-methyl-5,5-diphenyl)oxazaborolidine, 1,3,2-(4-isopropyl-5,5-diphenyl)oxazaborolidine, 1,3,2-(4-isobutyl-5,5-diphenyl)oxazaborolidine, 1,3,2-(2,4-dimethyl-5,5-diphenyl)oxazaborolidine, 1,3,2-(4-isopropyl-2-methyl-5,5-diphenyl)oxazaborolidine, 1,3,2-(4-isobutyl-2-methyl-5,5-diphenyl)oxazaborolidine, 1,3,2-(2,5,5-trimethyl-4-(tert.-butyl))oxazaborolidine, 1,3,2-(5,5-dimethyl-4-(tert.-butyl))oxazaborolidine, 1,3,2-(2,4-dimethyl-5,5-di(o-methylphenyl))oxazaborolidine, 1,3,2-(4-methyl-5,5-di(o-methylphenyl))oxazaborolidine, 1,3,2-(2,4-dimethyl-5,5-dibenzyl)oxazaborolidine, 1,3,2-(4-methyl-5,5-dibenzyl)oxazaborolidine, 1,3,2-(2,4-dimethyl-5,5-di(p-methoxyphenyl)oxazaborolidine, 1,3,2-(4-methyl-5,5-di(p-methoxyphenyl)oxazaborolidine, 3,4-propano-1,3,2-oxazaborolidine, 5,5-diphenyl-3,4-propano-1,3,2-oxazaborolidine, 2-methyl-5,5-diphenyl-3,4-propano-1,3,2-oxazaborolidine, 2-methyl-3,4-propano-1,3,2-oxazaborolidine, 2-ethyl-3,4-propano-1,3,2-oxazaborolidine, 5,5-diphenyl-3,4-ethano-2-methyl-1,3,2-oxazaborolidine, 3,4-butano-5,5-di(p-tolyl)-2-methyl-1,3,2-oxazaborolidine, and so on.

The optically active oxazaborolidine (II) can be prepared by reacting the optically active β-aminoalcohol (I) with a boronic acid of the formula (V):

wherein $R^6$ is the same as define above, or with a boroxine derivative of the formula (VI):

wherein $R^6$ is the same as defined above.

Examples of the groups for $R^6$ in the formulas (V) and (IV) are the same as those exemplified above.

Specific examples of the boronic acid (V) are boronic acid, methylboronic acid, ethylboronic acid, propylboronic acid, butylboronic acid, pentylboronic acid, hexylboronic acid, phenylboronic acid, α, β-naphthylboronic acid, o-, m- or p-methylphenylboronic acid, 2,3-, 2,4-, 2,5-, 2,6-, 3,4- or 3,5-dimethylphenylboronic acid, mesitylboronic acid, o-, m- or p-fluorophenylboronic acid, o-, m- or p-chlorophenylboronic acid, 2,3-, 2,4-, 2,5-, 2,6-, 3,4- or 3,5-difluorophenylboronic acid, benzylboronic acid, o-, m- or p-tolylmethylboronic acid, 2,3-, 2,4-, 2,5-, 2,6-, 3,4- or 3,5-dimethylbenzylboronic acid, and so on.

Specific examples of the boroxine derivative (VI) are trimethylboroxine, triethylboroxine, tripropylboroxine, tributylboroxine, triisobutylboroxine, tripentylboroxine, trihexylboroxine, trioctylboroxine, tris(1-methylethyl)boroxine, tris(1,1-dimethylethyl)boroxine, tris(1-methylpropyl)boroxine, tris(1,1-diethylpropyl)boroxine, tris(1-chloroethyl)boroxine, tris(3-chloropropyl)boroxine, tris(3,3,3-trifluoropropyl)boroxine, triphenylboroxine, tris(2-methylphenyl)boroxine, tris(3-methylphenyl)boroxine, tris(4-methylphenyl)boroxine, tris(2-ethylphenyl)boroxine, tris(3-ethylphenyl)boroxine, tris(4-ethylphenyl)boroxine, tris(2,3-dimethylphenyl)boroxine, tris(2,4-dimethylphenyl)boroxine, tris(2,5-dimethylphenyl)boroxine, tris(2,6-dimethylphenyl)boroxine, tris-(3,4-dimethylphenyl)boroxine, tris(3,5-dimethylphenyl)boroxine, tris(2-methoxyphenyl)boroxine, tris(3-methoxyphenyl)boroxine, tris(4-methoxyphenyl)boroxine, tris(2-ethoxyphenyl)boroxine, tris(2-propoxyphenyl)boroxine, tris(2-chlorophenyl)boroxine, tris(3-chlorophenyl)boroxine, tris(4-chlorophenyl)boroxine, tris(3-bromophenyl)boroxine, tris(3-fluorophenyl)boroxine, tris(4-chlorophenyl)boroxine, tris(4-bromophenyl)boroxine, tris(4-fluorophenyl)boroxine, tris(2,3-difluorophenyl)boroxine, tris(2,4-difluorophenyl)boroxine, tris(2,5-difluorophenyl)boroxine, tris(2,6-difluorophenyl)boroxine, tris(3,4-difluorophenyl)boroxine, tris(3,5-difluorophenyl)boroxine, tris(4-bromo-2,6-dimethylphenyl)boroxine, tris(4-bromo-3,5-dimethylphenyl)boroxine, tris(4-bromo-3,6-dimethylphenyl)boroxine, tris(2-chloro-5-methoxyphenyl)boroxine, tris(2-bromo-5-methoxyphenyl)boroxine, tris(2-fluoro-5-methoxyphenyl)boroxine, tris(5-bromo-2-methoxyphenyl)boroxine, tris(4-chloro-3-methoxyphenyl)boroxine, tris(4-ethoxy-2,3-difluorophenyl)boroxine, tris(2-(chloromethyl)phenyl)boroxine, tris(2-(bromomethyl)phenyl)boroxine, tris(4-(bromomethyl)phenyl)boroxine, tris(o-(1-bromoethyl)phenyl)boroxine, tris(m-(1-bromoethyl)phenyl)boroxine, tris(p-(1-bromoethyl)phenyl)boroxine, tris(p-(dibromomethyl)phenyl)boroxine, tris(m-(trichloromethyl)phenyl)boroxine, tris(o-(1,2-dibromoethyl)phenyl)boroxine, tris(2-(trifluoromethyl)phenyl)boroxine, tris(3-(trifluoromethyl)phenyl)boroxine, tris(4-(trifluoromethyl)phenyl)boroxine, tris(2-(bromomethyl)-6-methylphenyl)boroxine, tris(phenylethyl)boroxine, trichloroboroxine, tribromoboroxine, and so on.

In the preparation of the optically active oxazaborolidine (II), an amount of the boronic acid (V) is usually from 1 to 5 equivalents, preferably from 1 to 2 equivalents of the optically active β-aminoalcohol (I), or an amount of the boroxine derivative (IV) is usually from 0.3 to 1 equivalent, preferably from 0.3 to 0.8 equivalent of the optically active β-aminoalcohol (I).

In general, the above reaction is performed in the presence of a solvent. As the solvent, any aprotic solvent may be used. Examples of the solvent are aromatic hydrocarbons such as toluene, benzene, chlorobenzene, etc., aliphatic hydrocarbons such as hexane, heptane, chloroform, dichloroethane, etc., and so on.

A reaction temperature is usually from 0° to +150° C., preferably from 10° to 120° C., and a reaction time is usually from 10 minutes to 8 hours.

If desired, the optically active oxazaborolidine (II) may be isolated from the reaction mixture by a per se conventional method such as concentration, distillation, and so on.

In general, the optically active oxazaborolidine (II) and the metal borohydride are mixed in a solvent which is used in the reduction reaction.

An amount of the optically active oxazaborolidine (II) is usually from 0.01 to 0.6 mole per one mole of the prochiral ketone, or from 0.05 to 0.9 mole per one mole of the oxime derivative (IV).

Preferred examples of the metal borohydride are lithium borohydride, sodium borohydride, potassium borohydride, zinc borohydride, and so on. Among them, sodium borohydride is particularly preferred.

An amount of the metal borohydride is usually at least 0.5 mole, preferably from 0.5 to 1 mole in terms of boron atoms per one mole of the prochiral ketone, or usually from 0.5 to 2.5 moles, preferably from 0.7 to 2 moles in terms of boron atoms per one mole of the oxime derivative (IV).

Preparation of an optically active alcohol through reduction of a prochiral ketone The optically active alcohol can be prepared by reacting the prochiral ketone corresponding to the optically active alcohol and the acid with the mixture of the metal borohydride and i) the borane compound prepared from the optically active β-aminoalcohol (I) and the boron hydride, or from the optically active β-aminoalcohol (I), the metal borohydride and the acid, or ii) the optically active oxazaborolidine (II).

A preferred example of the prochiral ketone is a ketone of the formula:

$$R^7\text{—CO—}R^8 \qquad (VII)$$

wherein $R^7$ and $R^8$ are different and represent an alkyl group which may have a substituent, an aryl group which may have a substituent, or an aralkyl group which may have a substituent, or $R^7$ and $R^8$ form, together with a carbon atom of the carbonyl group, a ring or condensed ring optionally having a hetero atom.

When the reduction reaction is carried out using this prochiral ketone (VII), the corresponding optically active alcohol of the formula (VIII):

$$R^7\text{—}C^*H(OH)\text{—}R^8 \qquad (VIII)$$

wherein $R^7$ and $R^8$ are the same as defined above, and * stands for an asymmetric carbon atom is obtained.

The alkyl group for $R^7$ and $R^8$ has usually 1 to 6 carbon atoms and is optionally substituted with at least one halogen atom, and examples thereof are methyl, ethyl, propyl, butyl, pentyl, cyclopentyl, hexyl, cyclohexyl, chloromethyl, bromomethyl, dichloromethyl, trichloromethyl, difluoromethyl, trifluoromethyl, 2-chloroethyl, 3-chloropropyl, 4-chlorobutyl, and so on.

Examples of the aryl group for $R^7$ and $R^8$ are aromatic hydrocarbon groups having usually 6 to 15 carbon atoms and optionally at least one substituent such as phenyl, 1-naphthyl, 2-naphthyl, etc., and heterocyclic groups such as 2-pyridyl, 3-pyridyl, 4-thiazolyl, etc.

Examples of the substituent which is optionally present on the aryl group are halogen atoms (e.g. chlorine, bromine, etc.), lower alkyl groups (e.g. methyl, ethyl, propyl, butyl, etc.), lower alkoxy groups (e.g. methoxy, ethoxy, propoxy, etc.), aralkyl groups (e.g. benzyl, etc.), aralkyloxy groups (e.g. benzyloxy, etc.), a cyano group, lower haloalkyl groups having 1 to 6 carbon atoms (e.g. fluoromethyl, trifluoromethyl, chloromethyl, trichloromethyl, etc.).

Examples of the substituted aryl group are halogen-substituted phenyl (e.g. o-, m- or p-chlorophenyl, o-, m- or p-bromophenyl, 2,3-, 2,4-, 2,5-, 2,6-, 3,4- or 3,5- dichlorophenyl, etc.), lower alkyl-substituted phenyl (e.g. o-, m- or p-methylphenyl, o-, m- or p-ethylphenyl, o-, m- or p-propylphenyl, o-, m- or p-butylphenyl, 2,3-, 2,4-, 2,5-, 2,6-, 3,4- or 3,5-dimethylphenyl, etc.), lower alkoxy-substituted phenyl (e.g. o-, m- or p-methoxyphenyl, o-, m- or p-ethoxyphenyl, o-, m- or p-propoxyphenyl, etc.), benzyloxy-substituted phenyl (e.g. o-, m- or p-benzyloxyphenyl, etc.), cyano-substituted phenyl (e.g. o-, m- or p-cyanophenyl, etc.), 2-trifluoromethyl-4-thiazolyl, 2-methyl-4-thiazolyl, and so on.

The aralkyl group has usually 7 to 15 carbon atoms and optionally at least one substituent, and examples thereof are benzyl, o-, m- or p-tolylmethyl, o-, m- or p-ethylbenzyl, o-, m- or p-methoxybenzyl, o-, m- or p-ethoxybenzyl, and so on.

Examples of the ring or condensed ring formed from $R^7$ and $R^8$ together with the carbon atom of the carbonyl group are cyclic ketones such as cyclopentenone, cyclohexenone, 1,3-cyclopentanedione, 4-cyclopentene-1,3-dione, etc.; hetero atom-containing cyclic ketones such as 3-oxopyrrolidine, 3-oxopiperidine, 3-oxo-quinuclidine, and N-alkyl or N-aralkyl derivatives of the above cyclic ketones; indaline, tetralinone, and so on.

Examples of the prochiral ketone (VII) are acetophenone, propiophenone, butyrophenone, 1-acetonaphthone, 2-acetonaphthone, o-methoxyacetophenone, o-ethoxyacetophenone, o-propoxyacetophenone, o-benzyloxyacetophenone, p-tert.-butylacetophenone, 2-acetylpyridine, p-cyanoacetophenone, phenyl benzyl ketone, phenyl o-tolylmethyl ketone, phenyl m-tolylmethyl ketone, phenyl p-tolylmethyl ketone, 2-butanone, 2-pentanone, 2-hexanone, 2-heptanone, 2-octanone, cyclohexyl methyl ketone, cyclohexyl benzyl ketone, 2-chloroacetophenone, 2-bromoacetophenone, 2-bromo-3'-chloroacetophenone, 2-chloro-3'-chloroacetophenone, 2-bromo-3'-bromoacetophenone, 2-bromo-3'-fluoroacetophenone, 2-bromo-3'-methylacetophenone, 2-bromo-3'-ethylacetophenone, 2-bromo-3'-propylacetophenone, 2-bromo-3'-butylacetophenone, 2-bromo-3'-methoxyacetophenone, 2-bromo-3'-ethoxyacetophenone, 2-bromo-3'-propoxyacetophenone, 2-bromo-3'-butoxyacetophenone, 2-bromo-4'-chloroacetophenone, 2-bromo-4'-bromoacetophenone, 2-bromo-4'-fluoroacetophenone, 2-bromo-4'-methylacetophenone, 2-bromo-4'-ethylacetophenone, 2-bromo-4'-propylacetophenone, 2-bromo-4'-butylacetophenone, 2-bromo-4'-methoxyacetophenone, 2-bromo-4'-ethoxyacetophenone, 2-bromo-4'-propoxyacetophenone, 2-bromo-4'-butoxyacetophenone, 2-bromo-2'-chloroacetophenone, 2-bromo-2'-bromoacetophenone, 2-bromo-2'-fluoroacetophenone, 2-bromo- 2'-methylacetophenone, 2-bromo-2'-ethylacetophenone, 2-bromo-2'-propylacetophenone, 2-bromo-2'-butylacetophenone, 2-bromo-2'-methoxyacetophenone, 2-bromo-2'-ethoxyacetophenone, 2-bromo-2'-propoxyacetophenone, 2-bromo-2'-butoxyacetophenone, 2-bromo-2'-chloro-3'-methoxyacetophenone, 2-bromo-2'-bromo-3'-methoxyacetophenone, 2-bromo-2'-fluoro-3'-methoxyacetophenonone, 2-bromo-3'-methoxy-2'-methylacetophenone, 2-bromo-2',3'-dimethoxyacetophenone, 2-bromo-2'-ethoxy-3'-methoxyacetophenone, 2-bromo-2', 3'-dichloroacetophenone, 2-bromo-2'-bromo-3'-chloroacetophenone, 2-bromo-3'-chloro-2'-fluoroacetophenone, cyclopentenone, 1,3-cyclopentandione, cyclohexenone, 4-cyclopenten-1,3-dione, 3-oxopyrrolidine, 3-oxopiperidine, 3-oxoquinuclidine, N-alkyl or N-aralkyl derivatives thereof; 2-bromo-3'-chloro-2'-fluoroacetophenone, 2-bromo-3'-chloro-2'- methylacetophenone, 2-bromo-3'-chloro-2'-methoxyacetophenone, 2-bromo-3'-chloro-2'-ethoxyacetophenone, 2-bromo-3'-bromo-4'-chloroacetophenone, 2-bromo-2',4'-dibromoacetophenone, 2-bromo-2'-bromo-4'-fluoroacetophenone, 2-bromo-2'-bromo-4'-methylacetophenone, 2-bromo-2'-bromo-4'-methoxyacetophenone, 2-bromo-4'-chloro-2'-fluoroacetophenone, 2-bromo-2',4'-difluoroacetophenone, 2-bromo-4'-bromo-2'-fluoroacetophenone, 2-bromo-2'-fluoro-4'-methylacetophenone, 2-bromo-2'-fluoro-4'-methoxyacetophenone, 2-bromo-4'-ethoxy-2'-fluoroacetophenone, 2-bromo-4'-chloro-2'-ethoxyacetophenone, 2-bromo-4'-bromo-2'-ethoxyacetophenone, 2-bromo-4'-fluoro-2'-ethoxyacetophenone, 2-bromo-4'-methyl-2'-ethoxyacetophenone, 2-bromo-4'-methoxy-2'-ethoxyacetophenone, 2-bromo-2',4'-diethoxyacetophenone, 2-bromo-4'-chloro-3'-ethoxyacetophenone, 2-bromo-4'-bromo-3'-ethoxyacetophenone, 2-bromo-4'-fluoro-3'-ethoxyacetophenone, 2-bromo-3'-ethoxy-4'-methylacetophenone, 2-bromo-3'-ethoxy-4'-methoxyacetophenone, 2-bromo-3',4'-diethoxyacetophenone, 2-bromo-5'-bromo-3'-chloroacetophenone, 2-bromo-3',5'-dibromoacetophenone, 2-bromo-5'-bromo-3'-fluoroacetophenone, 2-bromo-5'-bromo-3'-methylacetophenone, 2-bromo-5'-bromo-3'-methoxyacetophenone, 2-bromo-5'-bromo-3'-ethoxyacetophenone, 2-bromo-3'-chloro-5'-ethoxyacetophenone, 2-bromo-3'-bromo-5'-ethoxyacetophenone, 2-bromo-5'-ethoxy-3'-fluoroacetophenone, 2-bromo-5'-ethoxy-3'-methylacetophenone, 2-bromo-5'-ethoxy-3'-methoxyacetophenone, 2-bromo-3',5'-dimethoxyacetophenone, 2-bromo-3',5'-diethoxyacetophenone, 2-bromo-3',5'-dichloroacetophenone, 2-bromo-3',5'-difluoroacetophenone, 2-bromo-2',6'-dichloroacetophenone, 2-bromo-2',4',6'-trichloroacetophenone, 2-bromo-3',4',5'-trichloroacetophenone. 4-bromoacetyl-2-methylthiazole, 4-bromoacetyl-2-trifluoromethylthiazole, and so on.

Examples of the acid are Brønsted acids such as sulfuric acid, acetic acid, phosphoric acid, methanesulfonic acid, p-toluenesulfonic acid, hydrogen chloride, etc.; and Lewis acids such as zinc chloride, boron trifluoride, aluminum chloride, aluminum bromide, titanium tetrachloride, tin tetrachloride, tin trichloride, etc.

An amount of the acid is usually from 0.8 to 1.2 equivalents, preferably from 0.9 to 1.1 equivalents of the metal borohydride in the mixture of the borane compound and the metal borohydride.

In general, the reduction reaction is performed in the presence of a solvent. Examples of the solvent are ethers (e.g. dioxane, tetrahydrofuran, diglyme, etc.), sulfides (e.g. dimethylsulfide, diethylsulfide, etc.), and mixtures thereof, and mixtures of the above solvent and a hydrocarbon (e.g. benzene, toluene, xylene, chlorobenzene, 1,2-dichloroethane, etc.).

An amount of the solvent is usually from 1 to 50 wt. parts per one wt. part of the oxime derivative.

The reduction of the prochiral ketone is carried out by reacting the prochiral ketone and the acid with the mixture of the metal borohydride and the borane compound or the optically active oxazaborolidine (II). Preferably, the prochiral ketone and the acid are dropwise added to the mixture of the metal borohydride and the borane compound or the optically active oxazaborolidine (II). In this case, the prochiral ketone and the acid may be added in admixture or separately. Alternatively, they may be added in the form of a solution in the solvent.

A reducing temperature is usually 150° C. or lower, preferably from −20° to 110° C., more preferably 0° to 100° C.

A time for dropwise adding the prochiral ketone and the acid is usually from 0.1 to 20 hours. After the dropwise addition of the prochiral ketone and the acid, the reaction mixture is preferably stirred for 0.1 to 10 hours while warming at a temperature in the above range.

The progress of the reaction can be monitored with an analytical method such as gas chromatography.

After the reduction reaction, the borane compound or the optically active oxazaborolidine (II) may be decomposed by the addition of an acid such as hydrochloric acid to the reaction mixture, and optionally the solvent is evaporated off. Then, to the reaction mixture, an extraction solvent such as toluene and an aqueous solution of an acid such as hydrochloric acid are added to separate an acid of the optically active β-aminoalcohol (I) with the acid, and the solvent is evaporated off from the separated organic layer to obtain the desired optically active alcohol in the salt form.

The separated salt of the optically active β-aminoalcohol (I) with the acid is made basic and extracted with an extraction solvent such as toluene, followed by evaporating the solvent off to recover the optically active β-aminoalcohol (I) in the free form.

The obtained optically active alcohol can be further purified by a per se conventional purification method such as distillation, chromatography, and so on.

Preparation of an optically active amine (III) by reduction of an oxime derivative (IV)

The optically active amine (III) can be prepared by reacting the oxime derivative (IV) and the acid with the mixture of the metal borohydride and i) the borane compound prepared from the optically active β-aminoalcohol (I) and the boron hydride, or from the optically active β-aminoalcohol (I), the metal borohydride and the acid, or ii) the optically active oxazaborolidine (II).

The oxime derivative (IV) may be an syn-form, an anti-form or a mixture thereof which is rich in one of them.

In the formula (IV), $R^7$ and $R^8$ are different and represent an alkyl group which may have at least one substituent, an aryl group which may have at least one substituent or an aralkyl group which may have at least one substituent, or $R^7$ and $R^8$ form, together with the carbon atom of the oxime group, a ring or condensed ring which may have a hetero atom.

Examples of the groups for each of $R^7$ and $R^8$ are the same as those exemplified in connection with the prochiral ketone (VI).

Examples of the ring or condensed ring formed from $R^7$ and $R^8$ together with the carbon atom of the oxime group are oxime ethers of cyclic ketones (e.g. cyclopentenone, cyclohexenone, etc.), cyclic ketones having a hetero atom (e.g. 3-oxopyrrolidine, 3-oxopiperidine, 3-oxoquinuclidine, N-alkyl or N-aralkyl derivatives thereof, etc.), and benzene-ring condensed cyclic ketones (e.g. indanone, tetralinone, etc.).

The alkyl group for $R^9$ has usually 1 to 10 carbon atoms, and examples thereof are methyl, ethyl, propyl, butyl, pentyl, cyclopentyl, hexyl, cyclohexyl, heptyl, cycloheptyl, octyl, nonyl, decyl, etc.

The aralkyl group for $R^9$ has usually 7 to 12 carbon atoms, and examples thereof are benzyl, β-phenethyl, naphthylmethyl, etc.

The alkyl-substituted silyl group has usually 3 to 12 carbon atoms in the alkyl substituents in total, and examples thereof are trimethylsilyl, dimethyl-tert.-butylsilyl, tri-n-propylsilyl, tri-n-butylsilyl, etc.

Specific examples of the oxime derivative (IV) are O-methyl, O-ethyl, O-octyl, O-cyclohexyl, O-benzyl, and O-trimethylsilyl derivatives of oximes of acetophenone, propiophenone, butyrophenone, 1-acetonaphthone, 2-acetonaphthone, o-, m- or p-methoxyacetophenone, o-ethoxyacetophenone, o-propoxyacetophenone, o-, m- or p-benzyloxyacetophenone, 2-acetylpyridine, p-cyanoacetophenone, phenyl benzyl ketone, phenyl o-tolylmethyl ketone, phenyl m-tolylmethyl ketone, phenyl p-tolylmethyl ketone, 2-butanone, 2-pentanone, 2-hexanone, 2-heptanone, 2-octanone, cyclohexyl methyl ketone, cyclohexyl benzyl ketone, 2-chloroacetophenone, p-tert.-butylacetophenone, p-chloroacetophenone, m-bromoacetophenone, p-bromoacetophenone, p-cyanoacetophenone, 2-chloro-3'-chloroacetophenone, m,p- or o,p-dichloroacetophenone, 3-sulfonamide-4-methoxybenzyl methyl ketone, 3,4-dimethoxybenzyl methyl ketone, 3'-benzyloxyacetophenone, isobutyl 2-piperidinophenyl ketone, cyclopentenone, cyclohexenone, pyrrolidin-2-one, pyrrolidin-3-one, piperidin-2-one, piperidin-3-one, quinuclidin-2-one, quinuclidin-3-one, 2-piperidylmethyl phenyl ketone, 8-methoxytetrahydronaphthalen-2-one, etc.

They may be the syn- or anti-form, or mixtures thereof in which either one of the syn-form and the anti-form is richer than the other.

The oxime derivative (IV) may be prepared from the above described prochiral ketone (III) according to a per se conventional method. When one of the syn-form and the anti-form, is used, the rest of them may be transformed to the necessary form by isomerization between the anti-form and the syn-form, whereby the raw material is effectively used.

Examples of the acid are Brønsted acids such as sulfuric acid, acetic acid, phosphoric acid, methanesulfonic acid, p-toluenesulfonic acid, hydrogen chloride, etc.; and Lewis acids such as zinc chloride, boron trifluoride, aluminum chloride, aluminum bromide, titanium tetrachloride, tin tetrachloride, tin trichloride, iodine, etc.

An amount of the acid is usually from 0.8 to 1.2 equivalents, preferably from 0.9 to 1.1 equivalents of the metal borohydride.

In general, the reduction reaction is performed in the presence of a solvent. Examples of the solvent are ethers (e.g. dioxane, tetrahydrofuran, diglyme, etc.), sulfides (e.g. dimethylsulfide, diethylsulfide, etc.), and mixtures thereof, and mixtures of the above solvent and a hydrocarbon (e.g. benzene, toluene, xylene, chlorobenzene, 1,2-dichloroethane, etc.).

An amount of the solvent is usually from 1 to 50 times the weight of the oxime derivative (III).

The reduction of the oxime derivative (IV) is carried out by reacting the oxime derivative (IV) and the acid with the mixture of the metal borohydride and the borane compound or the optically active oxazaborolidine (II). Preferably, the oxime derivative (IV) and the acid is added to the mixture of the metal borohydride and the borane compound or the optically active oxazaborolidine (II). In this case, they may be added in admixture or separately, or in the form of a solution in the solvent.

The reduction reaction can be accelerated by the use of a transition metal halide (e.g. cobalt chloride, nickel chloride, cesium chloride, etc.) in an amount of 0.1 to 5 mole % based on the oxime derivative (IV).

A reaction temperature is usually 150° C. or lower, preferably from −20° to +110° C., more preferably from 0° to 100° C.

A time for adding the oxime derivative and the acid is usually from 0.1 to 10 hours. After the addition of the oxime derivative and the acid, the reaction mixture is preferably stirred for 1 to 30 hours while warming at a temperature in the above range.

The progress of the reaction can be monitored with an analytical method such as gas chromatography.

After the reduction reaction, the borane compound or the optically active oxazaborolidine (II) may be decomposed by the addition of an acid such as hydrochloric acid to the reaction mixture, to obtain the optically active β-aminoalcohol (I) and the optically active amine (III), which are separated by utilizing a difference of their solubilities in a solvent, or distillation.

The obtained optically active amine (I) can be further purified by a per se conventional purification method such as recrystallization in the form of a salt with the acid, distillation, chromatography, and so on.

The optically active β-aminoalcohol separated can be recovered in the same manner as in the above chapter of "Preparation of optically active alcohol".

According to the present invention, the optically active alcohol having a high optical purity can be prepared by using the metal borohydride which is cheap and available in an industrial scale as a hydrogen source.

In addition, the amount of the used metal borohydride or boron hydride is decreased and the optically active alcohol is effectively prepared.

Further, the optically active amine is prepared effectively with decreasing the used amount of the metal borohydride or boron hydride as the hydrogen source.

EXAMPLES

The present invention will be illustrated by the following Examples, which will not limit the scope of the present invention in any way.

Example 1

Under a nitrogen atmosphere, sodium borohydride (0.38 g, 10 mmol) was suspended in a solution of (1S,2R)-(+)-norephedrine (0.151 g, 1 mmol) in dioxane (10 ml). To the suspension, a mixture of 96% sulfuric acid (0.102 g, 1 mmol) and dioxane (1 ml) was added, followed by stirring at 65° to 70° C. for 30 minutes to obtain a mixture of a borane compound and sodium borohydride.

To this mixture, a mixture of 96% sulfuric acid (0.408 g, 4 mmol), acetophenone (2.16 g, 18 mmol) and dioxane (20 ml) was dropwise added over 100 minutes at the same temperature, and then stirred for 30 minutes.

After cooling to room temperature, the 10% hydrochloric acid (20 ml) was added, and then the mixture was extracted with toluene (each 20 ml) twice. The organic layer was washed with water (each 20 ml) twice, and analyzed by gas chromatography to find that the conversion was 100%. The washed extract was also analyzed by high performance liquid chromatography (HPLC) using an optically active column to find that obtained optically active α-phenethyl alcohol consisted of 10.4% of the (R)-isomer and 89.6 % of the (S)-isomer.

Example 2

In the same manner as in Example 1 except that a mixture of 96% sulfuric acid (0.408 g, 4 mmol), acetophenone (2.16 g, 18 mmol) and dioxane (10 ml) was dropwise added while refluxing dioxane (101° C.), the reactions were performed.

The conversion was 100%, and the obtained optically active α-phenethyl alcohol consisted of 12.2% of the (R)-isomer and 87.8% of the (S)-isomer.

Example 3

In the same manner as in Example 1 except that tetrahydrofuran was used in place of dioxane, and the mixture was stirred for 30 minutes while refluxing tetrahydrofuran (65° C.) instead of the stirring at 65°–70° C. for 30 minutes, a mixture of the borane compound and sodium borohydride was prepared.

Then, in the same manner as in Example 1 except that a mixture of 96% sulfuric acid (0.408 g, 4 mmol), acetophenone (1.2 g, 10 mmol) and tetrahydrofuran (6 ml) was dropwise added over 60 minutes at the same temperature, and thereafter a mixture of acetophenone (1.2 g, 10 mmol) and tetrahydrofuran (6 ml) was dropwise added over 60 minutes, the reaction was performed.

The conversion was 92%, and the obtained optically active α-phenethyl alcohol consisted of 14.3% of the (R)-isomer and 85.7% of the (S)-isomer.

Example 4

In the same manner as in Example 1 except that (1R,2S)-2-amino-1,2-diphenylethanol (0.213 g, 1 mmol) was (1S,2R)-(+)-norephedrine, the reactions were performed.

The conversion was 100%, and the obtained optically active α-phenethyl alcohol consisted of 6.4% of the (R)-isomer and 93.6% of the (S)-isomer.

Example 5

In the same manner as in Example 1 except that (S)-α,α-diphenyl-2-pyrrolidinemethanol (0.253 g, 1 mmol) was used in place of (1S,2R)-(+)-norephedrine, the reactions were performed.

The conversion was 100%, and the obtained optically active α-phenethyl alcohol consisted of 3.2% of the (R)-isomer and 96.8% of the (S)-isomer.

Example 6

Under a nitrogen atmosphere, sodium borohydride (0.378 g, 10 mmol) was suspended in a solution of (1S,2R)-(+)-norephedrine (0.1512 g, 1 mmol) in dioxane (10 ml). To the suspension, a mixture of 100% sulfuric acid (0.098 g, 1 mmol) and dioxane (1 ml) was added over 10 minutes, followed by stirring at 75° to 80° C. for 1 hour to obtain a mixture of a borane compound and sodium borohydride.

To this mixture, a mixture of 100% sulfuric acid (0.392 g, 4 mmol), phenacyl chloride (1.546 g, 10 mmol) and dioxane (5 ml) was dropwise added over 15 minutes at the same temperature, and then stirred for 30 minutes at the same temperature.

After cooling to room temperature, the 10% hydrochloric acid (10 ml) was added, and then the mixture was extracted with toluene (each 20 ml) twice. The organic layer was washed with water (each 30 ml) twice to obtain a solution of optically active 2-chloro-1-phenylethanol in toluene.

The conversion was 100%, and the obtained optically active 2-chloro-1-phenylethanol consisted of 87.3% of the (R)-isomer and 12.7% of the (S)-isomer.

Example 7

In the same manner as in Example 6 except that (1S,2R)-2-amino-1-(2,5-dimethoxyphenyl)-1-propanol (1 mmol) was used in place of (1S,2R)-(+)-norephedrine, the reactions were performed.

The conversion was 100%, and the obtained optically active 2-chloro-1-phenylethanol consisted of 84.6% of the (R)-isomer and 15.4% of the (S)-isomer.

Example 8

In the same manner as in Example 6 except that (1S,2R)-2-amino-1-(2,5-dimethylphenyl)-1-propanol (1 mmol) was used in place of (1S,2R)-(+)-norephedrine, the reactions were performed.

The conversion was 100%, and the obtained optically active 2-chloro-1-phenylethanol consisted of 82.7% of the (R)-isomer and 17.3% of the (S)-isomer.

Example 9

In the same manner as in Example 6 except that (1S,2R)-1,2-diphenyl-2-aminoethanol (1 mmol) was used in place of (1S,2R)-(+)-norephedrine, the reactions were performed.

The conversion was 100%, and the obtained optically active 2-chloro-1-phenylethanol consisted of 84.5% of the (R)-isomer and 15.5% of the (S)-isomer.

Example 10

In the same manner as in Example 6 except that propiophenone was used in place of phenacyl chloride, 98% sulfuric acid was used in place of 100% sulfuric acid, and the mixture of the 98% sulfuric acid (4 mmol), propiophenone (10 mmol) and dioxane (5 ml) was dropwise added over 30 minutes, the reactions were performed.

The conversion was 100%, and the obtained optically active 2-chloro-1-phenylpropanol consisted of 19% of the (R)-isomer and 81% of the (S)-isomer.

Example 11

Under a nitrogen atmosphere, a solution of 1M borane-tetrahydrofuran complex (2 ml, 2 mmol) in tetrahydrofuran was added to a solution of (1S,2R)-(+)-norephedrine (0.1512 g, 1 mmol) in dioxane (8 ml) at 10° to 120° C., followed by stirring at 75° to 80° C. for 1 hour to obtain a borane compound.

In the borane compound solution, sodium borohydride (0.303 g, 8 mmol) was suspended at 45° to 50° C., and then, to the suspension, a mixture of 98% sulfuric acid (0.4 g, 4 mmol), propiophenone (1.342 g, 10 mmol) and dioxane (5 ml) was added over 35 minutes, followed by stirring at the same temperature for 30 minutes. Thereafter, the reaction mixture was post-treated in the same manner as in Example 6.

The conversion was 99.9%, and the obtained optically active 1-phenylpropanol consisted of 18.3% of the (R)-isomer and 81.7% of the (S)-isomer.

Example 12

Under a nitrogen atmosphere, sodium borohydride (0.0908 g, 2.4 mmol) was suspended in a solution of (R)-(−)-phenylglycinol (0.0274 g, 0.2 mmol) in tetrahydrofuran (10 ml). To the suspension, a solution of iodine (0.203 g, 0.8 mmol) in tetrahydrofuran (1 ml) was added over about 10 minutes, followed by stirring at 65° C. for 1.75 hours to obtain a mixture of a borane compound and sodium borohydride.

To this mixture, a mixture of iodine (0.203 g, 0.8 mmol), acetophenone (0.24 g, 2 mmol) and tetrahydrofuran (1 ml)

was dropwise added over 25 minutes, and stirred for 30 minutes at the same temperature.

After cooling to room temperature, the 10% hydrochloric acid (10 ml) was added, and then the mixture was extracted with toluene (each 20 ml) twice. The organic layer was washed with water (each 20 ml) twice to obtain a solution of optically active α-phenethyl alcohol in toluene.

The conversion was above 99.9%, and the obtained optically active (x-phenethyl alcohol consisted of 94.4% of the (R)-isomer and 5.6% of the (S)-isomer.

Example 13

In the same manner as in Example 13 except that (1S, 2R)-(+)-norephedrine (0.2 mmol) was used in place of (R)-(−)-phenylglycinol, the reactions were performed.

The conversion was above 99.9%, and the obtained optically active α-phenethyl alcohol consisted of 89.4% of the (R)-isomer and 10.6% of the (S)-isomer.

Comparative Example 1

In the same manner as in Example 10 except that a mixture of 98% sulfuric acid (4 mmol) and dioxane (4 ml) was dropwise added over 10 minutes in place of dropwise addition of the mixture of 98% sulfuric acid (4 mmol), propiophenone (10 mmol) and dioxane (5 ml) over 30 minutes, and the mixture of propiophenone (10 mmol) and dioxane (2 ml) was dropwise added over 10 minutes, and thereafter the mixture was stirred for 1.5 hours, the reactions were performed.

The conversion was 2.7%, and the obtained optically active 1-phenylpropanol consisted of 40.4% of the (R)-isomer and 59.6% of the (S)-isomer.

Example 14

Under a nitrogen atmosphere, sodium borohydride (0.167 g, 4.4 mmol) was suspended in a solution of (R)-5,5-diphenyl-2-methyl-3,4-propano-1,3,2-oxazaborolidine (0.1224 g, 0.44 mmol) in dioxane (5 ml) (manufactured by Aldrich). To the suspension, a mixture of 98% sulfuric acid (0.221 g, 2.2 mmol), propiophenone (0.651 g, 4.9 mmol) and dioxane (2.5 ml) was added over 30 minutes at 75° to 80° C., followed by stirring at the same temperature for 30 minutes.

After the above reaction, the 10% hydrochloric acid (8 ml) was added, and then the mixture was extracted with toluene (each 15 ml) twice. The organic layer was washed with water (each 20 ml) twice, and analyzed by gas chromatography to find that the conversion was 99.9%. The washed organic layer was also analyzed by high performance liquid chromatography (HPLC) using an optically active column to find that obtained optically active 1-phenyl-1-propanol consisted of 11.3% of the (R)-isomer and 88.7% of the (S)-isomer.

Comparative Example 2

In the same manner as in Example 14 except that the mixture of 98% sulfuric acid (2.2 mmol) and dioxane (1.5 ml) was dropwise added over 20 minutes instead of the dropwise addition of the mixture of 98% sulfuric acid (2.2 mmol), propiophenone (4.9 mmol) and dioxane (2.5 ml) over 30 minutes, and then the solution of propiophenone (4.9 mmol) in dioxane (1.5 ml) was dropwise added over 10 minutes, the reactions were performed.

The conversion was 2.6%, and the obtained optically active 1-phenylpropanol consisted of 48.2% of the (R)-isomer and 51.8% of the (S)-isomer.

Example 15

Under a nitrogen atmosphere, sodium borohydride (0.38 g, 10 mmol) was suspended in a solution of (1S,2R)-norephedrine (0.68 g, 4.5 mmol) in a mixed solvent of toluene and tetrahydrofuran (volume ratio=1:1) (10 ml) at room temperature. To the suspension, a solution of 100% sulfuric acid (0.245 g, 2.5 mmol) in a mixed solvent of toluene and tetrahydrofuran (volume ratio=1:1) (2.5 ml) was added over 20 minutes at room temperature, followed by stirring at 70° to 75° C. for 1 hour to obtain a mixture of a borane compound and sodium borohydride.

To this mixture, a solution of 100% sulfuric acid (0.245 g, 2.5 mmol) and anti-2',4'-dichloroacetophenone(O-methyl)oxime (1.09 g, 5 mmol) in a mixed solvent of toluene and tetrahydrofuran (volume ratio=1:1) (2.5 ml) was dropwise added over 30 minutes at 45° to 50° C., and stirred for 14 hours at the same temperature and then for 8 hours at 75° to 80° C.

After cooling to room temperature, the 10% hydrochloric acid (10 ml) was added, and then the mixture was made alkaline by the addition of a 20% aqueous solution of sodium hydroxide. Then, the mixture was extracted with toluene (each 15 ml) twice, and the organic layer was washed with water (each 15 ml) twice to obtain a solution of optically active (α-2',4'-dichlorophenylethylamine in toluene.

The conversion was 96.7%, and the obtained product contained 85.5% of α-2',4'-dichlorophenylethylamine and 14.5% of N-methoxy-α-2',4'-dichlorophenylethylamine. The optically active α-2',4'-dichlorophenylethylamine consisted of 93% of the (R)-isomer and 7% of the (S)-isomer.

Example 16

Under a nitrogen atmosphere, sodium borohydride (1.665 g, 0.044 mol) was suspended in a solution of (1S,2R)-norephedrine (6.05 g, 0.04 mol) in tetrahydrofuran (50 ml), and cooled to 10° C. To the suspension, a solution of 100% sulfuric acid (2.157 g, 0.022 mol) in tetrahydrofuran (50 ml) was added over 40 minutes at 10 to 15° C. Toluene (50 ml) was added and then the mixture was stirred at 70° to 75° C. for 1 hour to obtain a borane compound.

To this mixture which was cooled to 45° C., sodium borohydride (2.118 g, 0.056 g) was added and then a solution of 100% sulfuric acid (2.754 g, 0.028 ml) and anti-2',4'-dichloroacetophenone(O-methyl)oxime (10.9 g, 0.05 mol) in a mixed solvent of toluene and tetrahydrofuran (volume ratio=1:1) (30 ml) was dropwise added over 40 minutes at 45 to 50° C., and stirred for 3 hours at the same temperature and then for 8 hours at 75° to 80° C. Thereafter, cobalt chloride (0.0325 g) was added, and the mixture was further stirred for 3 hours at the same temperature.

After cooling to room temperature, the 10% hydrochloric acid (40 ml) was added, and then the mixture was made alkaline by the addition of a 20% aqueous solution of sodium hydroxide. Then, the mixture was extracted with toluene (each 40 ml) twice, and the organic layer was washed with water (each 40 ml) twice to obtain a solution of optically active α-2',4'-dichlorophenylethylamine in toluene.

The conversion was 98.3%, and the obtained product contained 99.8% of α-2',4'-dichlorophenylethylamine and 0.2% of N-methoxy-α-2',4'-dichlorophenylethylamine. The optically active α-2',4'-dichlorophenylethylamine consisted of 90.7% of the (R)-isomer and 9.3% of the (S)-isomer.

Example 17

In the same manner as in Example 15 except that (1S, 2R)-2-amino-1,2-diphenylethanol (0.96 g, 4.5 mmol) was used in place of (1S,2R)-norephedrine, the reactions were performed.

The conversion was above 99.9%, and the obtained product contained 96.4% of the amine compound and 3.6% of the N-methoxy derivative. The optically active compound consisted of 85.4% of the (R)-isomer and 14.6% of the (S)-isomer.

Example 18

In the same manner as in Example 15 except that (1S, 2R)-2-amino-1-(2,5-dimethoxyphenyl)propanol (0.89 g, 4.5 mmol) was used in place of (1S,2R)-norephedrine, the reactions were performed.

The conversion was 97.2%, and the obtained product contained 96.6% of the amine compound and 3.4% of the N-methoxy derivative. The optically active compound consisted of 86.5% of the (R)-isomer and 13.5% of the (S)-isomer.

Example 19

In the same manner as in Example 15 except that (1S, 2R)-2-amino-1-(2,5-dimethylphenyl)propanol (0.81 g, 4.5 mmol) was used in place of (1S,2R)-norephedrine, the reactions were performed.

The conversion was 96.3%, and the obtained product contained 96.8% of the amine compound and 3.2% of the N-methoxy derivative. The optically active compound consisted of 81.9% of the (R)-isomer and 18.1% of the (S)-isomer.

Example 20

Under a nitrogen atmosphere, a solution of 1M borane-tetrahydrofuran complex (4.5 ml, 4.5 mmol) was added to a solution of (1S,2R)-norephedrine (0.605 g, 4 mmol) in tetrahydrofuran (0.510 ml) and toluene (5 ml) at 10° to 15° C., followed by stirring at 75° to 80° C. for 1 hour to obtain a borane compound.

After cooling to room temperature, sodium borohydride (0.208 g, 5.5 mol) was added, and then a solution of 100% sulfuric acid (0.27 g, 2.75 mmol) and anti-2',4'-dichloroacetophenone(O-methyl)oxime (1.09 g, 5 mmol) in a mixed solvent of toluene and tetrahydrofuran (volume ratio=1:1) (5 ml) was dropwise added over 30 minutes at 45° to 50° C., followed by stirring at the same temperature for 14.5 hours, and then at 75° to 80° C. for 10 hours.

Thereafter, the reaction mixture was post-treated and analyzed in the same manner as in Example 15.

The conversion was 83.7%, and the obtained product contained 81.3% of the amine compound and 18.7% of the N-methoxy derivative. The optically active compound consisted of 92.8% of the (R)-isomer and 7.2% of the (S)-isomer.

Example 21

Under a nitrogen atmosphere, sodium borohydride (0.076 g, 2 mmol) was suspended in a solution of (1S,2R)-norephedrine (0.121 g, 0.8 mmol) in a mixed solvent of toluene and tetrahydrofuran (volume ratio=1:1) (2 ml). To the suspension, a solution of 98% sulfuric acid (0.045 g, 0.45 mmol) in a mixed solvent of toluene and tetrahydrofuran (volume ratio=1:1) (0.45 ml) was added over 10 minutes at 15° to 20° C., followed by stirring at 75° to 80° C. for 1 hour to obtain a mixture of a borane compound and sodium borohydride.

To this mixture, a solution of 98% sulfuric acid (0.055 g, 0.55 mmol) and p-tolylmethyl phenyl ketone(O-methyl) oxime (a ratio of anti-form to syn-form=93.5:6.5) (0.239 g, 1 mmol) in a mixed solvent of toluene and tetrahydrofuran (volume ratio=1:1) (0.55 ml) was dropwise added over 20 minutes at 45° to 50° C., and stirred for 19.5 hours at the same temperature and then for 10 hours at 75° to 80° C.

Thereafter, the reaction mixture was post-treated and analyzed in the same manner as in Example 15.

The conversion was 90.8%, and the obtained product contained 95.6% of 2-(p-tolyl)-1-phenylethylamine and 4.4% of N-methoxy-2-(p-tolyl)-1-phenylethylamine. The optically active 2-(p-tolyl)-1-phenylethylamine consisted of 88.9% of the (R)-isomer and 11.1% of the (S)-isomer.

Example 22

Under a nitrogen atmosphere, sodium borohydride (0.32 g, 8.5 mmol) was suspended in a solution of (R)-2-amino-1,1,3-triphenyl-1-propanol (0.68 g, 2.0 mmol) in a mixed solvent of toluene and tetrahydrofuran (volume ratio=1:1) (10 ml). To the suspension which was cooled to 10° C., a solution of 100% sulfuric acid (0.07 g, 0.75 mmol) in a mixed solvent of toluene and tetrahydrofuran (volume ratio=1:1) (1 ml) was added over 30 minutes at 10° to 15° C., followed by stirring at 45° to 50° C. for 1 hour to obtain a mixture of a borane compound and sodium borohydride.

To this mixture, a solution of 100% sulfuric acid (0.34 g, 3.5 mmol) and anti-2',4'-dichloroacetophenone(O-methyl) oxime (1.09 g, 5 mmol) in a mixed solvent of toluene and tetrahydrofuran (volume ratio=1:1) (2.0 ml) was dropwise added over 30 minutes at 45° to 50° C., and stirred for 5 hours at the same temperature and then for 14 hours at 75° to 80° C.

After cooling to room temperature, the 10% hydrochloric acid (10 ml) was added, and then the mixture was made alkaline by the addition of a 20% aqueous solution of sodium hydroxide. Then, the mixture was extracted with toluene (each 15 ml) twice, and the organic layer was washed with water (each 15 ml) twice.

The conversion was 100%, and the product contained 99.9% of α-2',4'-dichlorophenylethylamine and 0.1% of N-methoxy-α-2',4'-dichlorophenylethylamine.

The optically active α-2',4'-dichlorophenylethylamine consisted of 97.1% of the (R)-isomer and 2.9% of the (S)-isomer.

Example 23

In the same manner as in Example 22 except that (S)-2-amino-3-methyl-1,1-diphenyl-1-butanol (0.38 g, 1.5 mmol) was used in place of (R)-2-amino-1,1,3-triphenyl-1-propanol, the reactions were performed.

The conversion was 97.9%, and the obtained product contained 93.7% of the amine compound and 6.3% of the N-methoxy derivative. The optically active compound consisted of 97.0% of the (S)-isomer and 3.0% of the (R)-isomer.

Example 24

In the same manner as in Example 22 except that (S)-2-amino-4-methyl-1-pentanol (0.17 g, 1.5 mmol) was used in place of (R)-2-amino-1,1,3-triphenyl-1-propanol, the reactions were performed.

The conversion was 97.2%, and the obtained product contained 93.1% of the amine compound and 6.9% of the N-methoxy derivative. The optically active compound consisted of 90.5% of the (S)-isomer and 9.5% of the (R)-isomer.

Example 25

In the same manner as in Example 22 except that (S)-2-amino-3-methyl-1-butanol (0.16 g, 1.5 mmol) was used in place of (R)-2-amino-1,1,3-triphenyl-1-propanol, the reactions were performed.

The conversion was 97.6%, and the obtained product contained 86.2% of the amine compound and 13.8% of the N-methoxy derivative. The optically active compound consisted of 89.4% of the (S)-isomer and 10.6% of the (R)-isomer.

Example 26

Under a nitrogen atmosphere, sodium borohydride (0.32 g, 8.5 mmol) was suspended in a solution of (R)-2-amino-1,1-diphenyl-1-propanol (0.45 g, 2.0 mmol) in a mixed solvent of toluene and tetrahydrofuran (volume ratio=1:1) (10 ml). To the suspension which was cooled to 10° C., a solution of 100% sulfuric acid (0.07 g, 0.75 mmol) in a mixed solvent of toluene and tetrahydrofuran (volume ratio=1:1) (1 ml) was added over 30 minutes at 10 to 15° C., followed by stirring at 45° to 50° C. for 1 hour to obtain a mixture of a borane compound and sodium borohydride.

To this mixture, a solution of 100% sulfuric acid (0.34 g, 3.5 mmol) and anti-2',4'-dichloroacetophenone(O-methyl) oxime (1.09 g, 5 mmol) in a mixed solvent of toluene and tetrahydrofuran (volume ratio=1:1) (2.0 ml) was dropwise added over 30 minutes at 45° to 50° C., and stirred for 5 hours at the same temperature and then for 14 hours at 75° to 80° C.

After cooling to room temperature, the 10% hydrochloric acid (10 ml) was added, and then the mixture was made alkaline by the addition of a 20% aqueous solution of sodium hydroxide. Then, the mixture was extracted with toluene (each 15 ml) twice, and the organic layer was washed with water (each 15 ml) twice.

The conversion was 100%, and the product contained 99.9% of the amine compound and 0.1% of the N-methoxy derivative.

The optically active amine compound consisted of 97.1% of the (R)-isomer and 2.9% of the (S)-isomer.

Example 27

Under a nitrogen atmosphere, sodium borohydride (0.378 g, 10.0 mmol) was suspended in a solution of (R)-2-amino-1,1-diphenyl-1-propanol (0.909 g, 4.0 mmol) in tetrahydrofuran (10 ml). To the suspension which was cooled to 10° C., a solution of 100% sulfuric acid (0.22 g, 2.25 mmol) in tetrahydrofuran (1 ml) was added over 30 minutes at 10° to 15° C., followed by stirring at 45° to 50° C. for 1 hour to obtain a mixture of a borane compound and sodium borohydride.

To this mixture, toluene (5 ml) was dropwise added over 30 minutes at the same temperature, and then a solution of 100% sulfuric acid (0.27 g, 2.75 mmol) and 3'-methoxyacetophenone(O-methyl)oxime (a ratio of anti-form to syn-form=98.4:1.6) (0.896 g, 5 mmol) in a mixed solvent of toluene and tetrahydrofuran (volume ratio=2:1) (3.0 ml) was dropwise added over 45 minutes, and stirred for 19.5 hours at the same temperature and then for 7.5 hours at 75° to 80° C.

After cooling to room temperature, the 10% hydrochloric acid (10 ml) was added, and then the mixture was made alkaline by the addition of a 23% aqueous solution of sodium hydroxide. Then, the mixture was extracted with n-hexane (each 15 ml) twice, and the organic layer was washed with water (each 15 ml) twice.

The conversion was 99.9%, and the product contained 99.9% of α-3'-methoxyphenylethylamine and 0.1% of N-methoxy-α-3'-methoxyphenylethylamine.

The optically active α-3'-methoxyphenylethylamine consisted of 95.9% of the (R)-isomer and 4.1% of the (S)-isomer.

Example 28

In the same manner as in Example 27 except that (1S,2R)-2-amino-1-phenyl-1-propanol (0.605 g, 4.0 mmol) was used in place of (R)-2-amino-1,1-diphenyl-1-propanol, the reactions were performed.

The conversion was 99.3%, and the obtained product contained 89.0% of the amine compound and 11.0% of the N-methoxy derivative. The optically active compound consisted of 92.7% of the (R)-isomer and 7.3% of the (S)-isomer.

Example 29

In the same manner as in Example 27 except that (R)-2-amino-2-phenylethanol (0.605 g, 4.0 mmol) was used in place of (R)-2-amino-1,1-diphenyl-1-propanol, the reactions were performed.

The conversion was 95.3%, and the obtained product contained 98.6% of the amine compound and 1.4% of the N-methoxy derivative. The optically active compound consisted of 89.1% of the (R)-isomer and 10.9% of the (S)-isomer.

Example 30

Under a nitrogen atmosphere, sodium borohydride (0.121 g, 3.2 mmol) was suspended in a solution of (R)-5,5-diphenyl-2-methyl-3,4-propano-1,3,2-oxazaborolidine (0.333 g, 1.2 mmol) in a mixed solvent of toluene and tetrahydrofuran (volume ratio of 1:1) (5 ml) (manufactured by Aldrich). To the suspension, a solution of 98% sulfuric acid (0.16 g, 1.6 mmol) and anti-phenyl p-tolyl ketone(O-methyl)oxime (ratio of anti-form to syn-form=93.5:6.5) (0.383 g, 1.6 mmol) in a mixed solvent of toluene and tetrahydrofuran (volume ratio of 1:1) (3 ml) was added over 30 minutes at 45° to 50° C., followed by stirring at the same temperature for 4 hours, and then at 75° to 80° C. for 24 hours.

After the above reaction, the 10% hydrochloric acid (8 ml) was added, and then the mixture was extracted with toluene (each 10 ml) twice. The organic layer was washed with water (each 15 ml) twice to obtain a solution of (R)-1-phenyl-2-(p-tolyl)ethylamine in toluene.

The product was analyzed by gas chromatography to find that the conversion was 69.8% and the selectivity was 90.1%. The product was also analyzed by high performance liquid chromatography (HPLC) using an optically active column to find that obtained the optical purity was 51%(R).

Comparative Example 1

In the same manner as in Example 30 except that a solution of 98% sulfuric acid (1.6 mmol) in a mixed solvent of toluene and tetrahydrofuran (volume ratio of 1:1) (3 ml) was dropwise added over 30 minutes instead of the dropwise addition of the solution of 98% sulfuric acid (1.6 mmol) and anti-phenyl p-tolyl ketone(O-methyl)oxime (1.6 mmol) in a mixed solvent of toluene and tetrahydrofuran (volume ratio of 1:1) (1 ml), the reactions were performed.

The conversion was 50.9%, the selectivity was 76.5%, and the optical purity was 47.4%(R).

What is claimed is:

1. A process for preparing an optically active amine of the formula: (III):

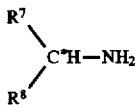

wherein $R^7$ and $R^8$ are different and represent an alkyl group which may have at least one substituent, an aryl group which may have at least one substituent or an aralkyl group which may have at least one substituent, or $R^7$ and $R^8$ form, together with the carbon atom bonded to the amino group, a ring or condensed ring which may have a hetero atom, and * is the same as defined above, comprising:

reacting an oxime derivative of the formula (IV):

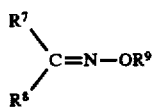

wherein $R^7$ and $R^8$ are the same as defined above, and $R^9$ is an alkyl group, an aralkyl group or an alkyl-substituted silyl group and an acid with a mixture which comprises (1) a boron-containing compound selected from the group consisting of (i) a borane compound which is obtained from an optically active β-aminoalcohol of the formula (I) and a boron hydride, or obtained from said optically active β-aminoalcohol (I), a metal borohydride and an acid, and (ii) an acid, and (ii) an optically active oxazaborolidine of the formula (II) and (2) a metal borohydride;

wherein the optically active β-aminoalcohol of the formula (I) is as follows:

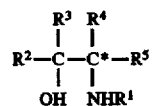

wherein $R^1$ is a hydrogen atom, a lower alkyl group or an aralkyl group which may have at least one substituent, $R^2$, $R^3$, $R^4$ and $R^5$ represent independently of each other a hydrogen atom, a lower alkyl group, an aryl group which may have at least one substituent, or an aralkyl group which may have a substituent, provided that $R^4$ and $R^5$ are different, that $R^1$ and $R^5$ may together form a lower alkylene group, or that $R^3$ and $R^4$ may together form a lower alkylene group which may optionally have a substituent or with which a benzene ring is condensed, and * stands for an asymmetric carbon atom, and a boron hydride, and wherein the optically active oxazaborolidine of the formula (II) is as follows:

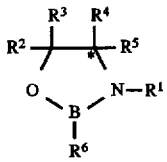

wherein $R^1$, $R^2$, $R^3$, $R^4$, $R^5$ and * are the same as defined above, and $R^6$ is a hydrogen atom, a halogen atom, an alkyl group which may be substituted by at least one halogen atom, an aryl group which may have at least on substituent or an aralkyl group which may have at least one substituent.

2. The process according to claim 1, wherein said oxime derivative (IV) is a syn-form, an anti-form or a mixture thereof which is rich one of them.

3. The process according to claim 1, wherein a mixture of said oxime derivative and said acid is reacted with said mixture of the borane compound and the metal borohydride.

4. The process according to claim 1, wherein said oxime derivative and said acid are added to said mixture of the borane compound and the metal borohydride separately.

5. The process according to claim 1, wherein a mixture of said oxime derivative and said acid is reacted with said mixture of the optically active oxazaborolidine and the metal borohydride.

6. The process according to claim 1, wherein said oxime derivative and said acid are added to said mixture of the optically active oxazaborolidine and the metal borohydride separately.

7. The process according to claim 1, wherein $R^7$ and $R^8$ are groups selected from the group consisting of an alkyl group which may have an substituent and an aryl group which may have a substituent.

8. The process according to claim 7, wherein $R^7$ and $R^8$ are groups selected from the group consisting of alkyl groups, halogenated alkyl groups, aryl groups, haloaryl groups, alkoxyalkyl-substituted aryl groups and aralkyloxy-substituted aryl groups.

9. The process according to claim 1, wherein said acid to be used together with said oxime derivative (IV) is at least one acid selected from the group consisting of Bronsted acids and Lewis acids.

* * * * *

UNITED STATES PATENT AND TRADEMARK OFFICE
CERTIFICATE OF CORRECTION

PATENT NO. : 5,801,280
DATED : September 1, 1998
INVENTOR(S) : Yoneyoshi et al.

Page 1 of 1

It is certified that error appears in the above-identified patent and that said Letters Patent is hereby corrected as shown below:

Column 23,
Line 31 and 32, please delete the phrase "and (ii) an acid,".

Signed and Sealed this

Twenty-first Day of August, 2001

Attest:

NICHOLAS P. GODICI
*Attesting Officer*   *Acting Director of the United States Patent and Trademark Office*